United States Patent [19]

Ramsay et al.

[11] Patent Number: 5,110,980
[45] Date of Patent: May 5, 1992

[54] SEPARATION OF POLY-β-HYDROXYALKANOIC ACID FROM MICROBIAL BIOMASS

[75] Inventors: Bruce A. Ramsay; Juliana Ramsay, both of Dollard des Ormeaux, Canada; Eric Berger, Auberives S/Varéze, France; Claude Chavarie, Montreal, Canada; Gerhart Braunegg, Graz, Austria

[73] Assignee: Ecole Polytechnique, Montreal, Canada

[21] Appl. No.: 409,758

[22] Filed: Sep. 20, 1989

[30] Foreign Application Priority Data

Apr. 6, 1989 [CA] Canada ................................ 595881

[51] Int. Cl.⁵ ............................................. C07L 69/66
[52] U.S. Cl. ..................... 560/185; 435/146; 435/259
[58] Field of Search ................. 435/146, 259; 560/185

[56] References Cited

U.S. PATENT DOCUMENTS

| | | | |
|---|---|---|---|
| 4,101,533 | 7/1978 | Lafferty et al. | 528/491 |
| 4,310,684 | 1/1982 | Vanlautem et al. | 560/185 |
| 4,324,907 | 4/1982 | Senior et al. | 560/185 |
| 4,336,334 | 6/1982 | Powell et al. | 435/146 |
| 4,358,583 | 11/1982 | Walker et al. | 528/491 |
| 4,391,766 | 7/1983 | Barham et al. | 264/210.1 |
| 4,910,145 | 3/1990 | Holmes et al. | 435/259 |

FOREIGN PATENT DOCUMENTS 0145233  6/1985  European Pat. Off. .

OTHER PUBLICATIONS

Nuti et al., Influence of phenylacetic acid on poly-β-hydroxybutyrate (PHB) polymerization and cell elongation in Azotobacter chroococcum, Beij, *Canadian J. of Microbiol.*, 18:1257–1261 (1972).

Dawes et al., The Role and Regulation of Energy Reserve Polymers in Micro-organisms, *Adv. Microbiol. Physiol.*, 10:135–266 (1973).

The Isolation and Estimation of the Poly-β-Hydroxy-y-Butyrate Inclusions of Bacillus Species, Williamson et al, J. Gen. Microbiol. 19, 198–203, (1958).

Characterization of Poly-β-Hydroxybutyrate Extracted from Different Bacteria, Lundgren, D. C., et al, Journal of Bacteriology, Jan. 1965, vol. 89, No. 1, pp. 245–251.

*Primary Examiner*—Paul J. Killos
*Attorney, Agent, or Firm*—Foley & Lardner

[57] ABSTRACT

Hypochlorite digestion of bacterial biomass to recover intracellular poly-β-hydroxylalkanoic acid (PHA) has not been used on a large scale since it has been widely reported to severely degrade the polymer. The process of the invention proposes to optimize the initial biomass concentration, the digestion time and pH of the hypochlorite solution to minimize degradation. Consequently, PHA of up to 95% purity with an average molecular weight of 600,000 can be recovered from biomass initially containing PHA having a molecular weight of 1,200,000. By incorporating a pretreatment step with an anionic surfactant solution, PHA of 99% purity with a molecular weight of $1.20 \times 10^6$ was obtained from biomass containing 57% PHA by weight with an initial molecular weight of $1.25 \times 10^6$.

16 Claims, 2 Drawing Sheets

SEPARATION OF POLY-β-HYDROXYALKANOIC ACID FROM MICROBIAL BIOMASS

BACKGROUND OF THE INVENTION

1. Field of the Invention

The present invention relates to a process for the separation of poly-β-hydroxyalkanoic acid (PHA) of high molecular weight from a microbial, PHA-producing biomass, by treatment with hypochlorite either alone or in combination with a surfactant.

2. Background of the Art

Poly-β-hydroxyalkanoic acid (PHA) is an optically active linear polyester made of various small β-hydroxymonocarboxylic acids. It can be produced synthetically but is more cheaply produced by microorganisms. Many micro-organisms accumulate large quantities of PHA intracellularly when their growth is limited by some element other than carbon. The excess carbon is converted into PHA as a mechanism of carbon and energy storage. The form of PHA most commonly produced by microorganisms is a homopolymer of β-hydroxybutyric acid. This homopolymer is called poly-β-hydroxybutyric acid (PHB). Many PHB-accumulating microorganisms will produce PHA copolymers if certain organic acids such as propionic acid are added to their medium during the PHA accumulation phase.

Since PHA is an intracellular product, one of the limitations to the economic feasibility of its production is the cost of separating the PHA from the rest of the microbial biomass. Many methods have been developed to achieve this but they all have serious drawbacks.

A number of solvent extraction processes have been developed to separate PHA from its native biomass. These usually involve the use of chlorinated solvents such as chloroform (U.S. Pat. No. 4,324,907 and U.S. Pat. No. 4,358,583), dichloroethane (U.S. Pat. No. 4,391,766 and U.S. Pat. No. 4,324,907) or 1,1,2-trichloroethane (U.S. Pat. No. 4,310,684). Propylene or ethylene carbonate (U.S. Pat. No. 4,101,533) has also been used. Apart from being expensive, these processes generally involve working with large quantities of toxic and/or explosive volatile solvents. Moreover, in most of the cases, the PHA that has been extracted, must be subsequently precipitated by addition of the extracting solution to an alcohol such as methanol. In the case of propylene carbonate, PHB is soluble up to 340 g/L at 150° C. but to only 3 g/L at 100° C. Therefore cooling is used to obtain the purified polymer. In practice cells are often spray or freeze-dried before extraction. They may also be washed with acetone to remove polar lipids and excess water which may interfere with the extraction process.

European laid-open patent application (EP-A 0,145,233) discloses an expensive and complicated method comprising a thermal treatment of the PHA containing-biomass, followed by an enzymatic treatment and then a washing with an anionic surfactant to dissolve the cellular, non-PHA biomass.

A less complex method is also disclosed by Williamson and Wilkinson (J. Gen. Microbiol. 19:198-203 (1958)), in which the biomass is subjected to differential digestion by the sodium hypochlorite solution. Although simple and effective, this method however has been avoided up to now because it has been reported to cause severe degradation of the PHA molecular weight (Lundgren et al, J. Bacteriol. 89:245-251 (1965); Nuti et al, Can. J. Microbiol. 18:1257-1261 (1972); Dawes and Senior, Adv. Microbiol. Physiol. 10:135-266 (1973)). As a matter of fact the highest molecular weight which has been reported to have been obtained by this method was 22,000 (Lundgren et al, J. Bacteriol.89:245-251 (1965)).

OBJECTS OF THE INVENTION

An object of the present invention is to provide a process for the separation of PHA from a PHA-producing biomass, wherein the biomass is subjected to differential digestion using a hypochlorite solution to do so as is disclosed by Williamson and Wilkinson, but under such controlled and optimized conditions that it allows recovery of PHA having a high or very high molecular weight (over 100,000) which is equal to or higher than 50% of the molecular weight of the original PHA contained in the cells.

The invention is based on the discovery that, contrary to the general knowledge in this very particular field, differential digestion of a PHA-producing biomass with a hypochlorite solution is not as degradative as it was thought and reported with respect to the molecular weight of the resulting PHA, provided however that the digestion time and/or respective concentrations of biomass and hypochlorite be adjusted and/or controlled as a function of the desired purity.

Another object of the invention is also to provide a process for the separation of high molecular weight PHA from a PHA-producing biomass, wherein the biomass is first treated with a surfactant solution and subsequently subjected to a finishing, differential digestion using a hypochlorite solution to do so.

A further object of the invention is to provide a separation process of the above mentioned type, which is cheaper and simpler than those previously described and yet permits to obtain very high molecular weight PHA from a microbial biomass.

SUMMARY OF THE INVENTION

More particularly, the invention generally proposes a process for the separation of poly-β-hydroxy-alkanoic acid (PHA) of high molecular weight from a microbial, PHA-producing biomass, which process comprises the steps of adding a given amount of the biomass to a hypochlorite solution at a pH of 9 to 13.5, allowing this hypochlorite solution to digest the biomass for a given period of time, and recovering the non-digested PHA that remains in suspension from the hypochlorite solution.

In accordance with the invention, this process of separation of PHA by differential digestion of a PHA-containing biomass is improved over the prior art known to the Applicants in that, in a first step, a predetermined percentage of desired purity for the PHA to be recovered is fixed and then:

either the actual percentage of purity is determined as a function of time while the biomass is subjected to digestion, and the non-digested biomass is separated as soon as the predetermined percentage of desired purity is achieved, or the ratio of the initial hypochlorite concentration in the solution to the concentration of biomass added to this solution is adequately selected, usually by means of pretesting, to make sure that the dissolving capacity of the hypochlorite solution is exhausted when the predetermined percentage of desired purity is achieved.

In both cases, it has been found that little further degradation of the PHA molecular weight occurs and that, accordingly, substantial amounts of high or very high molecular weight PHA of very high purity (at least 85%) may be recovered.

In use, the conditions of the hypochlorite treatment can be manipulated to obtain PHA of a purity of up to 100% and/or a molecular weight equal to at least 50% and preferably over 80% of the original molecular weight of the PHA produced in the cells.

The conditions of pH, concentration of the hypochlorite solution, ratio of dissolving capacity of the hypochlorite solution to biomass, and treatment time play important roles. For example, it is possible to recover 90% of the PHA with 90% purity and conserve 67% of the original molecular weight (i.e. having a molecular weight of 800,000) by adding 1% biomass containing 65% PHA by weight, to a 5.25% hypochlorite solution at pH 10 for 40 min. On the other hand, it is possible to obtain a product of 100% purity but with a lower molecular weight of 535,000 if a 10.5% hypochlorite solution is used for 1 h as in the above example.

In accordance with a preferred embodiment of the invention, the hypochlorite solution used for the digestion is advantageously at pH 10 and the ratio of the initial hypochlorite concentration to the non-PHA biomass concentration in the solution is ranging from 3 to 35 and more preferably from 11 to 18, the most preferred ratio being 15.

The digestion is preferably carried out at ambient temperature or above, as lower temperatures have proved to slow down the digestion rate.

In accordance with another preferred embodiment of the invention, the process comprises the additional steps of pretreating the biomass by adding it to an aqueous solution containing a surfactant which is preferably anionic and recovering the biomass from said aqueous solution of surfactant, prior to adding it to the hypochlorite solution.

Preferably the ratio of the anionic surfactant concentration in the aqueous solution is ranging from 0.1 to 4.7 and is more preferably lower than 0.6 and the pretreatment time is of about 15 minutes at a pH of about 10. Then, the subsequent digestion may be as short as 1 minute.

GENERAL DESCRIPTION OF THE INVENTION

Tests carried out by the Applicants have shown that the rate of biomass digestion with a hypochlorite solution is increased when the hypochlorite concentration or temperature is increased. However, the molecular weight which is obtained for a particular degree of desired purity is fixed for an optimal ratio of hypochlorite to non-PHA biomass. If this ratio is too high, degradation of PHA will continue after maximum purity has been obtained.

Figure 1:
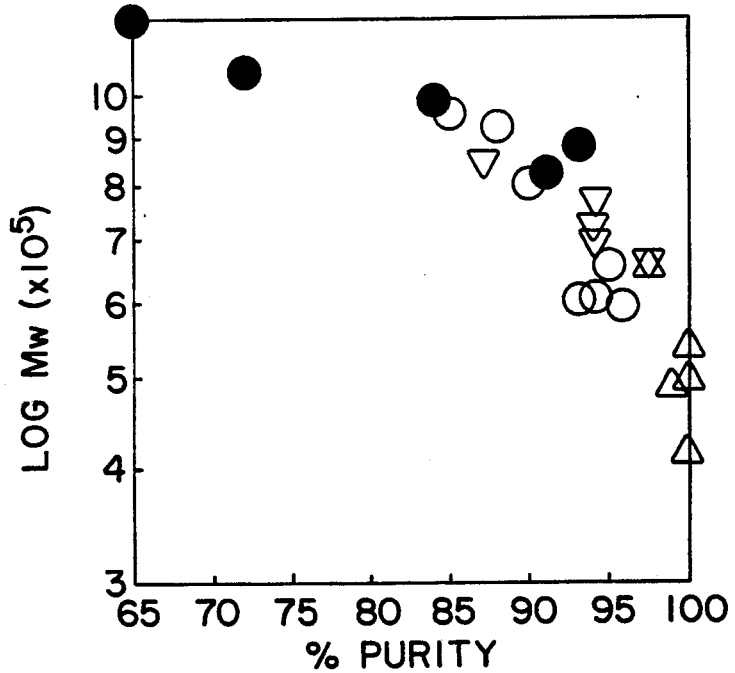
FIG. 1 is a curve showing the variation of the molecular weight of the recovered PHA as a function of its purity at different temperatures of digestion and concentrations of hypochlorite.

FIG. 1 illustrates this behaviour after hypochlorite treatment at pH 10 under a variety of conditions as described in Examples 3 to 6. Here it is seen that when the purity of the recovered PHA increases, the molecular weight of this PHA decreases. This particular behaviour is always true, even when the hypochlorite concentration is fixed (at 5.25% or 10.5%) and the digestion time is increased—see data (•) obtained at 0° C. and (0) obtained at 25° C. with a hypochlorite concentration of 5.25% and data (Δ) obtained at 25° C. with a hypochlorite concentration of 10.5%; or the hypochlorite concentration is increased and the digestion time is fixed (to 1 hour)—see data ▽ obtained at 25° C.

Hence, the key factor in using hypochlorite digestion to obtain PHA of both high purity and high molecular weight is to immediately separate the PHA from the hypochlorite solution as soon as the desired purity has been achieved or to balance the ratio of the initial hypochlorite concentration to non-PHA biomass concentration in the solution such that when the desired purity is achieved, the dissolving capacity of the hypochlorite solution is exhausted and little further degradation of the PHA molecular weight may occur.

In accordance with the invention, it has also been found that if a surfactant solution is added before hypochlorite treatment, the molecular weight of the recovered PHA may be conserved even further. For example, if a solution of 0.125% surfactant solution at pH 10 is followed by treatment with the 5.25% hypochlorite solution also at pH 10, 96% of the original molecular weight will be conserved to obtain 98% pure PHA having a molecular weight as high as 1,200,000. However, surfactant treatment on its own is insufficient to obtain PHA of high purity.

In all cases, one the non-PHA biomass has been dissolved, the PHA granules can be recovered by various methods, e.g. centrifugation, filtration, etc. Depending on the final purity required, the granules can be washed with water and/or acetone or dissolved in chloroform and then precipitated with alcohol.

Any kind of hypochlorite may be used to prepare the digesting solution. Thus, by way of example, use can be made of sodium, potassium or calcium hypochlorite.

Any kind of anionic surfactant may also be used to prepare the surfactant solution. Thus, by way of example, use can be made of any surfactant already used in the known PHA extraction processes making use of a surfactant. In the tests carried out by the Applicant, use was made of sodium dodecyl sulfate as surfactant (this compound is the one found in most of the powder detergents such as TIDE ®).

EXAMPLES

In all the following examples, the operational conditions were as follows unless otherwise indicated.

Production of PHA-containing biomass *Alcaligenes eutrophus* DSM 545 was produced in a 35L Bioengineering airlift reactor at 30° C. and a pH 7.0. The composition of the initial growth medium was 48 g/L glucose, 12.32 g/l (NH$_4$)SO$_4$, 2.5 g/L Na$_2$HPO$_4$. 2H$_2$O, 832 mg/L KH$_2$PO$_4$, 100 mg/L CacCl$_2$. H$_2$O, 200 mg/L MgSO$_4$. H$_2$O, 60 mg/L ammonium iron (III) citrate, 10 mg/L ZnSO$_4$. 7H$_2$O, 3 mg/L MnCl2 . 4H$_2$O, 30 mg/L H$_3$BO$_3$, 20 mg/L CoCl$_2$. 6H$_2$O, 1 mg/L CuSO$_4$. 5H$_2$O, 2 mg/L NiCl$_2$ . 6H$_2$O and 3 mg/L NaMo$_4$ . 2H$_2$O. When the glucose and ammonium were nearly exhausted, they were replaced by a concentrated solution to give a final concentration of 30 g/L glucose and 3 g/L NH$_4^+$. When these again neared exhaustion, concentrated glucose was added in a fed-batch mode until the cellular poly-$\beta$-hydroxybutyric acid concentration was at least 65% by weight.

Digestion of the biomass by hypochlorite

Hypochlorite solutions were prepared according to the method of Williamson and Wilkinson (see above). After adding the PHA-containing biomass to the hypochlorite solution, PHA was separated from the aqueous portion (containing residual biomass) by centrifugation at 4000×g for 15 min. The PHA was rinsed with water, recentrifuged and 5 volumes of acetone wa added to it. Granules of PHA were recovered by filtration.

Chloroform extraction of PHA

Acetone-washed biomass was mixed with 10 volumes of chloroform for 48 h at 25° C. Non-PHA biomass was removed by filtration and the polymer recovered by ethanol precipitation and filtration.

PHA analysis

PHA samples were prepared according to the method of Braunegg et al (1978). The resulting methylesters were quantified using a Hewlett-Packard* 5890 GC equipped with a flame ionization detector, and a HP5 capillary column which was 25 m long with a diameter of 0.2 $\mu$m. Separation was achieved with a temperature profile where initial temperature=90° C., final temperature=150° C., initial holding time=1 min, final holding time=1 min, and rate of temperature increase=8° C./min. Internal and external standards were benzoic and $\beta$-hydroxybutyric acids respectively.
* trademark

Molecular weight determination

The molecular weight determination was done at 30° C. by gel permeation chromatography using three 10 $\mu$m PL Gel mixed bed columns (Polymer Laboratories Inc., Amherst, Mass.) connected to a Spectra-Physics®8430 RI detector and a 4290 integrator equipped with a GPC plus chip. Fifty $\mu$L of sample (0.5% w/v) or narrow-cut polystyrene standard (0.5% w/v) dissolved in chloroform were analysed. Chloroform was used as the mobile phase at a flow rate of 1.6 mL/min. The Mark-Houwink constants for polystyrene (K=4.9×10$^5$ and a=0.794 (Dawkins, 1968)) and PHB (K=1.18×10$^4$ and a=0.78 (Akita et al, 1976)) were used in the universal calibration method (Grubisic et al, 1967; Majid et al, 1987).

In all the examples, the concentration of biomass, hypochlorite and surfactant are expressed in g/100 ml.

EXAMPLE 1

In examples 1 to 6, the PHA content in the cells was 65% by weight. One percent *Alcaligenes eutophus* biomass was added to a 5.25% hypochlorite solution at different pH's for 1 h at 25° C.

The molecular weights of the recovered PHA were analysed by gel permeation chromatography while purity was determined by gas chromatography as explained hereinabove. The weight average molecular weight of the chloroform extracted PHA was 1,200,000.

TABLE 1

|  | pH | | | |
|---|---|---|---|---|
|  | 8 | 10 | 12 | 13.6 |
| % purity | 70 | 90 | 90 | 98 |
| % PHA recovered | 77 | 90 | 90 | 78 |
| % MW* | 36 | 54 | 37 | 21 |
| MW (× 10$^5$ g/mole) | 4.36 | 6.50 | 4.39 | 2.50 |

% MW* is the percentage of the molecular weight of the PHA recovered to that of the chloroform extracted sample.

As can be seen for the results presented in Table 1, the higher is the pH, the higher is the purity that can be obtained. However at pH 10, there is an optimum with reasonably high purity and amount of PHA recovered with a minimum of degradation in molecular weight.

These data also show has if the hypochlorite to biomass ratio is reduced PHA of high molecular weight may still be obtained at higher PH's.

EXAMPLE 2

To a 5.25% hypochlorite solution at pH 10, various concentration of biomass were treated for 1 h.

Figure 2:
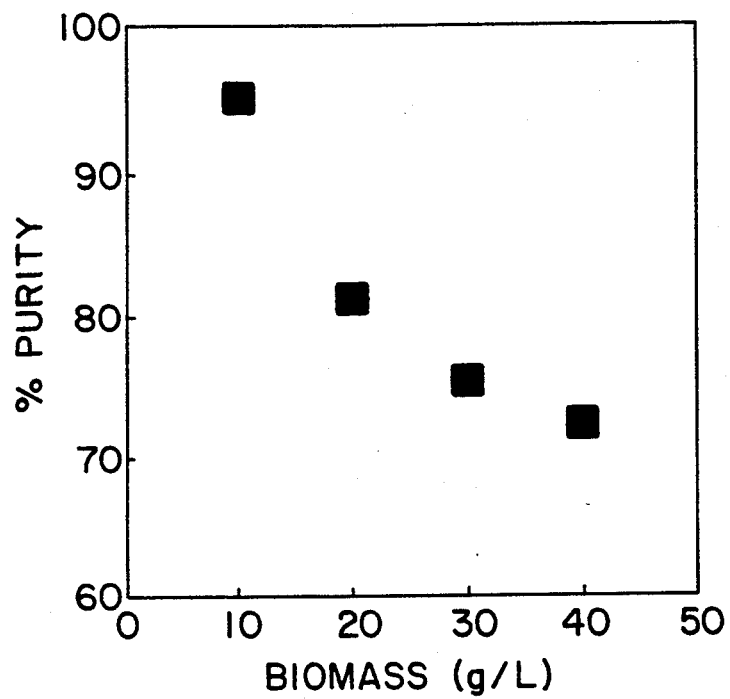
FIG. 2 is a curve showing the variation of the percentage of purity of the recovered PHA as a function of the concentration of biomass in the solution.

The results presented in Table 2 and reported in FIG. 2 show that as the concentration of biomass increases, the purity and the amount of PHA recovered decrease.

TABLE 2

|  | % biomass | | | |
|---|---|---|---|---|
|  | 1 | 2 | 3 | 4 |
| % purity | 95 | 81 | 75 | 72 |
| & PHA recovered | 95 | 83 | 79 | 79 |

EXAMPLE 3

One percent biomass was added to a 5.25% hypochlorite solution at pH 10 for varying lengths of times at 25° C.

Figure 3:
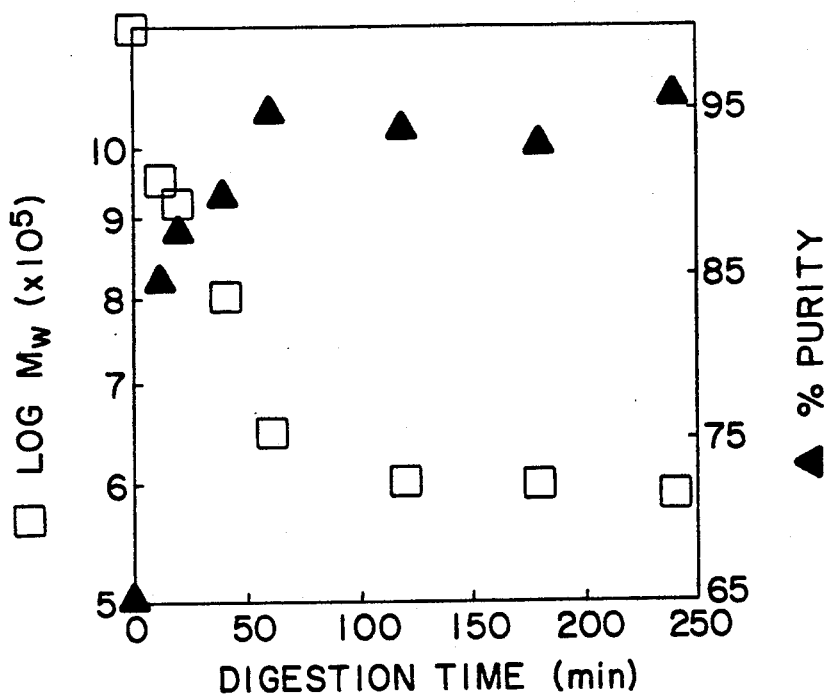
FIG. 3 is a curve showing the variations of the molecular weight and purity of the recovered PHA, respectively, as a function of the digestion time.

The results given in Table 3 and reported in FIG. 1—see (O) marks—and FIG. 3 show that once the biomass-dissolving capacity of the hypochlorite solution was exhausted the rate of loss in the molecular weight of the recovered PHA decreased. After complete exhaustion a plateau was reached, where the molecular weight remained almost constant.

Accordingly, suitable predetermination of the biomass dissolving capacity of a hypochlorite solution to treat a given amount of biomass, can be made and used subsequently at an industrial scale to separate PHA with a very high purity while making sure that the recovered PHA has a predetermined, very high molecular weight (over 50% of the original one).

TABLE 3

| Time (min) | Purity (%) | PHA recovered (%) | MW (× 10$^5$ g/mole) | MW* (%) |
|---|---|---|---|---|
| 12 | 85 | 89 | 9.53 | 79.4 |
| 20 | 88 | 90 | 9.20 | 76.7 |
| 40 | 90 | 90 | 8.0 | 66.7 |
| 60 | 95 | 93 | 6.5 | 54.2 |
| 120 | 94 | 90 | 6.0 | 50 |
| 180 | 93 | 83 | 6.0 | 50 |
| 240 | 96 | 86 | 5.9 | 49.2 |

EXAMPLE 4

This example is the same as example 3 except that the temperature was 0° C.

When the results given in Table 4 and reported in FIG. 1—see (•) marks—are compared with those in Table 3, it is seen that at a lower temperature, the rate of digestion is much slower than at 25° C.

TABLE 4

| Time (min) | Purity (%) | MW (× 10⁵ g/mole) | MW* (%) |
|---|---|---|---|
| 15 | 72 | 10.5 | 87.5 |
| 20 | 84 | 9.8 | 81.7 |
| 40 | 93 | 8.8 | 73.3 |
| 60 | 91 | 8.2 | 68.3 |

EXAMPLE 5

This example is the same as example 3 except that the concentration of hypochlorite was 10.5%.

Figure 4:
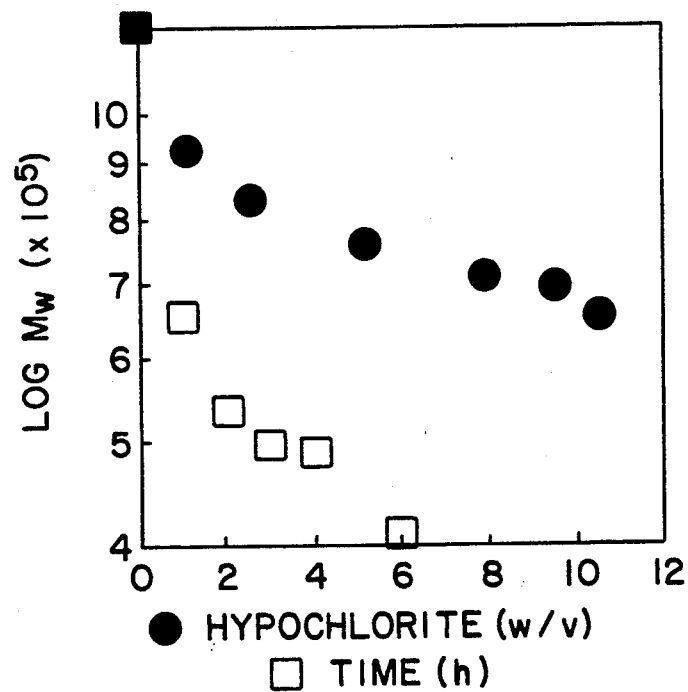
FIG. 4 is a curve showing the variations of the molecular weight of the recovered PHA as a function of the hypochlorite concentration and time, respectively.

The results in Table 5 and reported in FIG. 1 —see (Δ) marks—and FIG. 4 —see (□) Marks—, show that after the 0 h mark, PHA close to 100% purity was recovered. These results also show the molecular weight substantially decreases and not adjusted for fast exhaustion.

TABLE 5

| Time (h) | Purity (%) | MW (× 10⁵ g/mole) | MW* (%) |
|---|---|---|---|
| 1 | 97.5 | 6.54 | 54.5 |
| 2 | 100 | 5.35 | 44.6 |
| 3 | 100 | 4.95 | 41.3 |
| 4 | 99 | 4.87 | 40.6 |
| 6 | 100 | 4.10 | 34.2 |

EXAMPLE 6

One percent biomass was added to varying concentrations of hypochlorite solutions at pH 10 for 1 h.

As the concentration of hypochlorite increased, the purity increased but the resulting molecular weight decreased as seen in Table 6 and reported in FIG. 1—see ( ) marks—and FIG. 4—see (•) marks—.

TABLE 6

| Hypochlorite concentration | Purity (%) | MW (× 10⁵ g/mole) | MW* (%) |
|---|---|---|---|
| 1.1 | 86 | 9.25 | 77.1 |
| 2.6 | 87 | 8.33 | 69.4 |
| 5.2 | 94 | 7.60 | 63.3 |
| 7.9 | 94 | 7.10 | 59.2 |
| 9.5 | 94 | 6.93 | 57.8 |
| 10.5 | 97.5 | 6.54 | 54.5 |

EXAMPLE 7

In examples 7 to 11, the PHA content of the cells was 57% by weight and the chloroform extracted sample has a weight average molecular weight of 1,250,000.

One percent biomass was added to a 0.25% anionic surfactant solution (made up from TIDE® powder detergent) at varying pH's for 1 h.

Results presented in Table 7 show that although the purity and PHA recovered were low, the resulting molecular weight remained high.

TABLE 7

| | pH | | | |
|---|---|---|---|---|
| | 8 | 9 | 10 | 11 |
| % purity | 77 | 81 | 82 | 84 |
| % PHA recovered | 67 | 67 | 62 | 59 |
| % MW* | 92.5 | 92 | 86 | 82 |
| MW (× 10⁵ g/mole) | 11.57 | 11.47 | 10.70 | 10.02 |

EXAMPLE 8

One percent biomass was added to varying surfactant concentrations at pH 10.

Results presented in Table 8 show that as the concentration of surfactant increased the purity increased but the molecular weight and the amount of PHA recovered decreased.

TABLE 8

| | surfactant concentration % | | | |
|---|---|---|---|---|
| | 0.25 | 0.5 | 1 | 2 |
| % purity | 82 | 88 | 84 | 91 |
| % PHA recovered | 62 | 58 | 48 | 46 |
| % MW* | 86 | 86.5 | 84 | 77 |
| MW (× 10⁵ g/mole) | 10.70 | 10.80 | 10.49 | 9.64 |

EXAMPLE 9

After 1% biomass was added to a 0.25% surfactant solution for 15 min at different pHs, cells were recovered by centrifugation, treated with a 5.25% hypochlorite solution at pH 10 for 1 min. Results are presented in Table 9.

The purity and amount of PHA recovered were higher in this example than with biomass treated with only surfactant in Example 7. The loss in molecular weight was less than with the biomass treated with only hypochlorite as seen in Example 1. Moreover, it may be appreciated that this process is very fast as both steps lasted 16 minutes.

TABLE 9

| | pH | | |
|---|---|---|---|
| | 8 | 9 | 10 |
| % purity | 99 | 98 | 99 |
| % PHA recovered | 85 | 83 | 75 |
| % MW* | 82 | 90 | 96 |
| MW (× 10⁵ g/mole) | 10.01 | 11.50 | 12.00 |

EXAMPLE 10

The example is the same as example 9 except that the surfactant concentration was varied and the pH was kept constant at 10.

The results in Table 10 show that the lower is the surfactant concentration, the higher is the molecular weight recovered.

TABLE 10

| | surfactant concentration (%) | | | | |
|---|---|---|---|---|---|
| | 0.125 | 0.25 | 0.5 | 1 | 2 |
| % purity | 98 | 99 | 95 | 99 | 100 |
| % PHA recovered | 74 | 75 | 72 | 75 | 75 |
| % MW* | 96 | 96 | 88 | 80 | 88 |
| MW (× 10⁵ g/mole) | 12 | 12 | 11 | 10 | 11 |

EXAMPLE 11

Different concentrations of biomass were treated with 0.25% surfactant at pH 10 for 15 min followed by 1 min of treatment with hypochlorite solution.

The results expressed in Table 11 show that to recover a high purity of PHA using this concentration of surfactant, a low biomass concentration should be used.

TABLE 11

| | Biomass concentration (%) | | | | | |
|---|---|---|---|---|---|---|
| | 1 | 2 | 2.5 | 3 | 4 | 5 |
| % purity | 99 | 94 | 90 | 84 | 80 | 76 |
| % PHA recovered | 74 | 76 | 77 | 76 | 84 | 82 |

All the above examples show that when either the temperature or the hypochlorite concentration increases, the rate of biomass digestion also increases. However changing these conditions does not alter the molecular weight that may be obtained at a particular degree of purity (see FIG. 1).

If greater than 1.0% biomass is treated with a 5.25% hypochlorite solution, the purity of the obtained PHA diminishes (see FIG. 2).

Kinetic experiments also show that once the biomass-dissolving capacity of the hypochlorite solution is exhausted (as indicated by a drop in the rate of increased of purity), the rate of $M_w$ loss greatly decreases (see FIG. 3). On the other hand, when higher hypochlorite to biomass concentration ratios are used, the rate of PHB degradation remains high well after maximum-purity had been obtained. This can be seen in FIG. 4 where all samples after the 0 h mark had close to 100% PHA purity. Therefore if both high purity and high $M_w$ are required either the biomass to hypochlorite ratio must be optimized or the PHA must be rapidly separated from the hypochlorite solution as soon as the desired purity is achieved. Otherwise the PHA will continue to degrade after maximum purity has been achieved.

In all cases, it is worth mentioning that even when the cells were exposed to 10.5% (w/v) hypochlorite for up to 6 h, the molecular weight did not decrease to the low levels reported in the literature. Thus, the hypochlorite method for PHA purification is not as destructive as has been reported and it is even less so when the conditions of digestion are optimized.

The embodiments of the invention in which an exclusive property or privilege is claimed are defined as follows:

1. In a process for the separation of poly-β-hydroxyalkanoic acid (PHA) of high molecular weight from a bacterial, PHA-producing biomass, with said high molecular weight being equal to or at least 50% of the original molecular weight of said PHA produced in said biomass, said process comprising the steps of adding a given amount of said biomass to a hypochlorite solution at a pH of 9 to 13.5, allowing said hypochlorite solution to digest said biomass for a given period of time, and recovering the non-digested PHA that remains in suspension from said hypochlorite solution, the improvement consisting of:
   a) fixing a predetermined actual percentage of purity for the PHA to be recovered; and
   b) then carrying out a sequence of steps selected from the group consisting of
      (i) determining the actual percentage of purity as a function of time while said biomass is subject to digestion, and separating the non-digested biomass as soon as said predetermined percentage of desired purity is achieved, and
      (ii) selecting the ratio of the initial hypochlorite concentration in said solution to the concentration of biomass added to said solution such that the dissolving capacity of said hypochlorite solution is exhausted when said predetermined percentage of desired purity is achieved
   whereby, in both (i) and (ii), little further degration of said PHA molecular weight occurs.

2. The improved process of claim 1, wherein the hypochlorite solution is at a pH of about 10.

3. The improved process of claim 2, wherein the ratio of the initial hypochlorite concentration to the biomass concentration in the solution is ranging from 3 to 35.

4. The improved process of claim 3, wherein the concentration of biomass into the hypochlorite solution is equal to about 1% (expressed in gram per 100 ml).

5. The improved process of claim 3, wherein the predetermined percentage of purity is fixed to be at least 85%, the ratio of the initial hypochlorite concentration to the non-PHA biomass concentration in the solution is equal to about 15 and the digestion time is of at least 10 minutes at ambient temperature.

6. The improved process of claim 3, wherein the predetermined percentage of purity is fixed to be at least 90%, the ratio of the initial hypochlorite concentration to the non-PHA biomass concentration in the solution is equal to about 15 and the digestion time is of at least 40 minutes at ambient temperature.

7. The improved process of claim 3, wherein the predetermined percentage of purity is fixed to be at least 95%, the ratio of the initial hypochlorite concentration to the non-PHA biomass concentration in the solution is equal to about 15 and the digestion time is of about one hour at ambient temperature.

8. The improved process of claim 3, wherein the predetermined percentage of purity is fixed to be at least 85% and the digestion time is lower to or equal to one hour at ambient temperature.

9. The improved process of claim 3, comprising the additional steps of pretreating the biomass by adding it to an aqueous solution containing a surfactant and recovering said biomass from said aqueous solution of surfactant, prior to adding said biomass to the hypochlorite solution.

10. The improved process of claim 9, wherein the ratio of the surfactant concentration to the non-PHA biomass concentration in the aqueous solution is ranging from 0.1 to 4.7.

11. The improved process of claim 10, wherein:
   the predetermined time is of about 15 minutes;
   the ratio of the initial hypochlorite concentration to the non-PHA biomass concentration in the solution is ranging from 11 to 18,
   the digestion time is of about 1 minute.

12. The improved process of claim 11, wherein:
   the ratio of the surfactant concentration to the non-PHA biomass concentration in the aqueous solution is equal to or lower than 0.60; and
   the aqueous solution is at a pH of about 10.

13. The improved process of claim 12, wherein the surfactant is anionic.

14. The improved process of claim 1, comprising the additional steps of pretreating the biomass by adding it to an aqueous solution containing a surfactant and recovering said biomass from said aqueous solution of surfactant, prior to adding said biomass to the hypochlorite solution.

15. The improved process of claim 14, wherein the ratio of the surfactant concentration to the non-PHA biomass concentration in the aqueous solution is ranging from 0.1 to 4.7.

16. The improved process of claim 15, wherein:

the predetermined time is of about 15 minutes;
the ratio of the initial hypochlorite concentration to the non-PHA biomass concentration in the solution is ranging from 11 to 18,
the digestion time is of about 1 minute.

* * * * *